(12) United States Patent
Depue et al.

(10) Patent No.: US 6,897,309 B2
(45) Date of Patent: May 24, 2005

(54) PROCESS FOR HYDROXYAZAPIRONES

(75) Inventors: Jeffrey Depue, Hillsborough, NJ (US);
Atul S. Kotnis, Kendall Park, NJ (US);
Simon Leung, Piscataway, NJ (US);
Eric D. Dowdy, San Mateo, CA (US);
Daniel J. Watson, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 13 days.

(21) Appl. No.: 10/636,070

(22) Filed: Aug. 7, 2003

(65) Prior Publication Data

US 2004/0067958 A1 Apr. 8, 2004

Related U.S. Application Data

(60) Provisional application No. 60/402,759, filed on Aug. 12, 2002.

(51) Int. Cl.$^7$ ............................................. C07D 401/14
(52) U.S. Cl. ........................................................ 544/330
(58) Field of Search ........................................... 544/330

(56) References Cited

U.S. PATENT DOCUMENTS

| | | |
|---|---|---|
| 6,150,365 A | 11/2000 | Mayol |
| 6,593,331 B2 | 7/2003 | Camborde et al. |
| 2003/0022899 A1 | 1/2003 | Yevich et al. |
| 2003/0055063 A1 | 3/2003 | Yevich et al. |

FOREIGN PATENT DOCUMENTS

| | | |
|---|---|---|
| WO | WO 01/45687 A2 | 6/2001 |
| WO | WO 02/16347 A1 | 2/2002 |

*Primary Examiner*—Venkataraman Balasubramanian
(74) *Attorney, Agent, or Firm*—James Epperson

(57) ABSTRACT

This invention describes a process for preparing hydroxyazapirones of Formula I from azapirones of Formula II. The process comprises treating azapirones with a strong base, monitoring enolate formation of the azapirone by IR spectroscopy, and reacting the enolate with a source of molecular oxygen in the presence of a reductant. The process is suitable for large scale production of hydroxyazapirones.

22 Claims, No Drawings

PROCESS FOR HYDROXYAZAPIRONES

CROSS-REFERENCE TO RELATED APPLICATIONS

This application claims the benefit of U.S. provisional application No. 60/402,759, filed Aug. 12, 2002.

BACKGROUND OF THE INVENTION

Certain azapirones, such as the compounds of Formula II, have been shown to have therapeutic potential when hydroxylated to form hydroxyazapirones of Formula I. Two examples of hydroxyazapirones are 6-hydroxybuspirone ($R^1$ and $R^2$ are 1,4-butandiyl and n is 4) and 3-hydroxygepirone ($R^1$ and $R^2$ are methyl and n is 4). Initially discovered as metabolites (see Mayol et al. *Clin. Pharmacol. Ther.* 1985 37, 210 and Kerns et al. *J. Pharmaceut and Biomedical Analysis* 1999 20, 115–128), these compounds are now believed to be biologically active and their use in treating anxiety disorders and depression has been disclosed (Mayol, R. F. U.S. Pat. No. 6,150,365, 2000; Rider, P. H. PCT appl. WO 02/16347, 2002). As these compounds show promise in therapy, improved methods for their production would be of benefit.

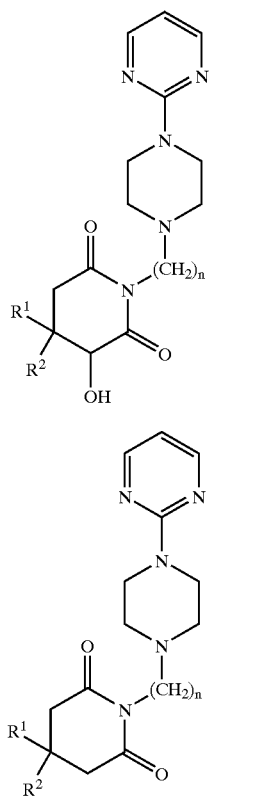

Processes which selectively hydroxylate Formula II azapirones into Formula I hydroxyazapirones have been disclosed (Mayol, R. F. U.S. Pat. No. 6,150,365, 2000; Rider, P. H. PCT appl. WO 02/16347, 2002). One process for hydroxylating both buspirone and gepirone is illustrated in Scheme 1. In this process, the imide enolate derived from imide II was generated and trapped by di-4-nitrobenzyl peroxydicarbonate [(PNBOCO)$_2$] to produce intermediate X. After chromatographic purification, hydrogenation of intermediate X afforded the Formula I compound.

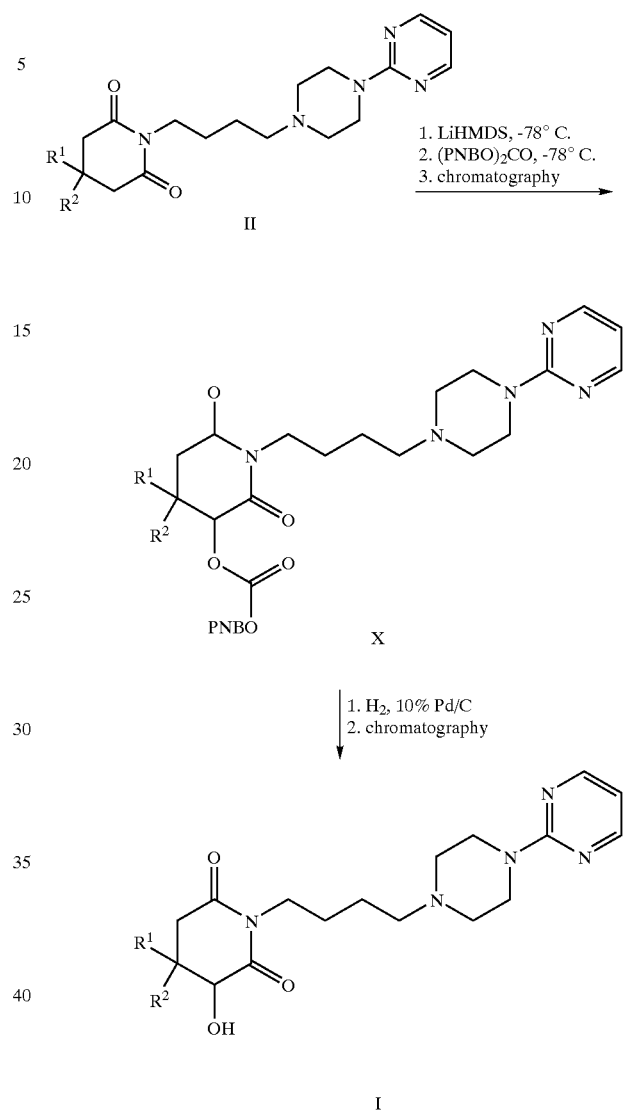

A second process, shown in scheme 2, was employed for buspirone hydroxylation. In this process, the imide enolate derived from II was reacted with 2-(phenylsulfonyl)-3-phenyloxaziridine (the Davis reagent) to form the postulated intermediate V. Acidic workup provided the Formula I product.

Drawbacks of both these processes include the requirement to synthesize the starting reagents and the necessity of chromatographically purifiying the products.

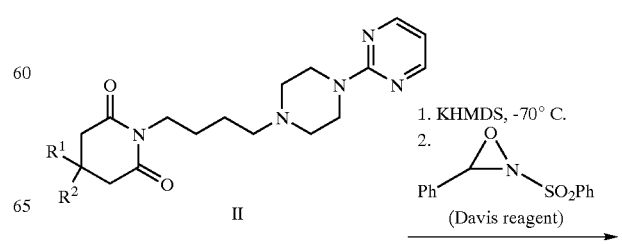

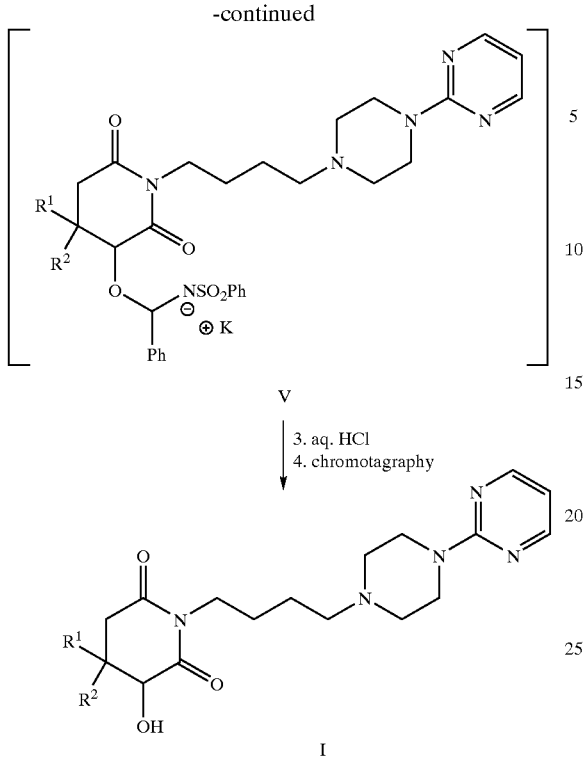

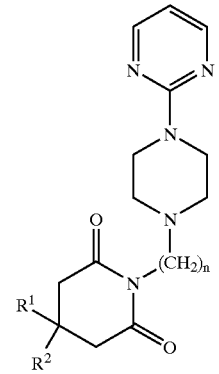

A third process involving enzymatic conversion in certain mammalian liver microsomes was not amenable to large-scale synthesis.

By contrast, the invention disclosed below improves upon these processes by employing a one step procedure using commercially available reagents and air. The process also provides direct crystallization of the product rather than chromatographic purification.

SUMMARY OF THE INVENTION

This invention describes an improved one-pot process for hydroxylation of certain useful azapirone psychtropic agents, such as buspirone and gepirone. The process uses commercially available reagents and air. The pure product is crystallized directly from the reaction mixture, and the process is amenable to large-scale synthesis.

DETAILED DESCRIPTION OF THE INVENTION

The invention provides a process for the preparation of hydroxyazapirones of Formula I,

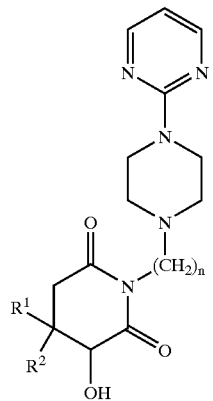

wherein $R^1$ and $R^2$ are independently hydrogen or $C_{1-6}$alkyl, or where $R^1$ and $R^2$ taken together are —$CH_2(CH_2)_{0-5}CH_2$—, and n is an integer from 2 to 5, from azapirones of Formula II.

The process is shown in scheme 3. Briefly, a Formula II azapirone compound is dissolved in an appropriate solvent containing 1–5 equivalents of a suitable reductant. A strong base is added, generating an imide enolate of Formula III. A source of oxygen is added until the generation of Formula I compound is complete. In the course of the experimental workup, the product is crystallized and isolated. This process is described in detail below.

Scheme 3.

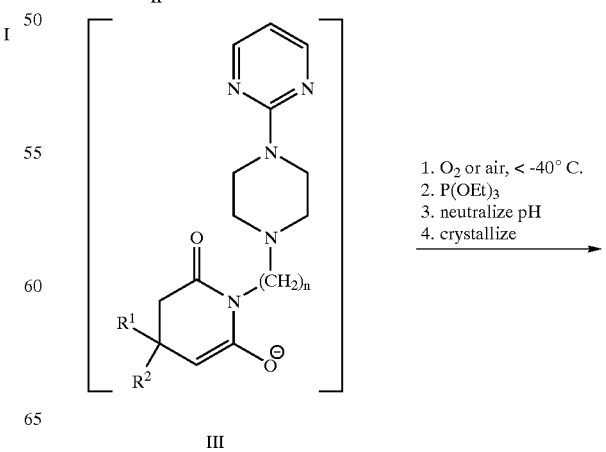

-continued

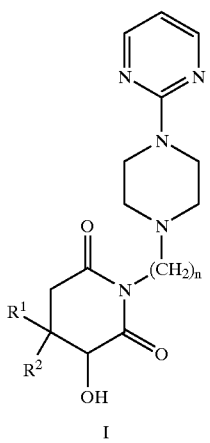

A Formula II compound is dissolved in a suitable aprotic solvent to a preferred ratio of 10–20 mL/g. Suitable solvents for enolate generation include ethereal solvents such as diethylether, 1,2-dimethoxyethane, dioxane, and 2-methyltetrahydrofuran. Tetrahydrofuran (THF) is a preferred solvent for this reaction. A suitable reductant in the range of 1–5 equivalents is added to the solution. Suitable reductants are those that reduce organic hydroperoxides to alcohols. These reductants include tri($C_{1-8}$)alkylphosphites as well as other reductants such as triarylphosphites, triaryl- and trialkyl phosphines, thiourea, sodium borohydride, copper (II) chloride with iron (II) sulfate, iron (III) chloride, titanium isopropoxide, dimethyl sulfide, diethyldisulfide, sodium sulfite, sodium thiosulfate, zinc and acetic acid, and 1-propene. While the reductant may be added at any convenient stage of the process, it is preferably present when the oxygenation reaction proceeds. The solution is cooled to –40 to –100° C., preferably to a range of –68 to –75° C., and allowed to completely stabilize.

About one equivalent of an appropriate strong base is added. The base mediates deprotonation and formation of an imide enolate anion (III). Preferred bases suitable for this type of deprotonation include disilazanes, such as lithium bis(trimethylsilyl)amide, sodium bis(trimethylsilyl)amide, and potassium bis(trimethylsilyl)amide. Other strong bases which may be used include dialkylamine bases (such as lithium diisopropylamide), metal hydrides, and metal alkoxides.

Generation of a stoichiometric amount of enolate is critical for optimizing the process-undergeneration of enolate resulted in poor conversion and recovered starting material, while overaddition of base resulted in the production of dihydroxylated side products. The use of reaction monitoring, in particular employing FTIR, to directly observe conversion of the starting imide to the corresponding enolate solved this issue. Direct observation of anion generation allowed the base to be charged until the IR signal for starting material no longer declined, indicating complete consumption of the starting material. Starting material was then incrementally charged until a steady IR signal of starting material was observed, indicating no excess base was present. This provided a solution of enolate with a slight excess of starting material (1% to 3%). Because excess starting material was easier to purge than dihydroxylated side products (the impurities that resulted when excess base was present), this was the preferred situation. Variations in the base titer, water content, and phosphite quality were automatically corrected because the phosphite was charged before the base.

In general, the enolate compound of Formula III was formed in situ and reacted immediately with an electrophile. However, the invention includes stable enol compounds which can later be reactivated. For example, enol acetates and enolsilanes are suitable substrates for the process.

After enolate generation, air or oxygen was sparged into the reaction mixture, controlling the initial rate of sparging to maintain the temperature of the reaction mixture less than –40° C. The sparging was continued until the reaction was complete as indicated by HPLC. Although air and oxygen gas are preferred sources of molecular oxygen, other oxygen sources can be used including gaseous mixtures containing molecular oxygen, liquid oxygen, and solutions containing liquid oxygen.

The mixture was diluted with a suitable solvent such as methyl tert-butylether (MTBE), ethyl acetate, or 2-methyl-THF, warmed to room temperature, and neutralized with 1M hydrochloric acid until the pH was 6.0 to 7.0, preferably 6.5 to 6.9. Other acids can be used and the final pH can also be adjusted with various bases including sodium phosphate. The reaction mixture was then partitioned, and the organic layer separated. The organic solvents were replaced by isopropanol, and the solution was cooled to crystallize the product. The product was normally isolated in 64–90% with greater than 95% purity.

Occasionally the reaction product contained recovered starting material or a 6,10-dihydroxylated side product. In these cases, one of two crystallization procedures improved the purity. These procedures are described in the Specific Embodiments section.

DESCRIPTION OF THE SPECIFIC EMBODIMENTS

EXAMPLE 1

6-Hydroxybuspirone

Buspirone (8-[4-[4-(2-pyrimidinyl)-1-piperazinyl]butyl]-8-azaspiro(4.5)-decane-7,9-dione) (246.5 g, 639.6 mmol) was charged to a 12 L flask equipped with a mechanical stirrer and a React-IR probe under inert gas. Tetrahydrofuran (4.383 kg, 60.8 mol, 4.930 L, 20 mL/g) was charged and the mixture agitated at ambient temperature until homogeneous. Triethyl phosphite (371.9 g, 2.238 mol, 383.8 mL, 3.5 eq) was added and the mixture cooled to –68 to –75° C. The mixture was agitated at this temperature for at least 10 minutes to allow the React-IR signal to stabilize. 1.0 M Sodium bis(trimethylsilyl)amide in THF (600.4 g, 664.1 mmol, 664.1 mL, 1.00 eq) was charged to the mixture at such a rate so as to maintain the temperature less than –60° C. Small amounts of sodium bis(trimethylsilyl)amide were charged to the mixture until the IR signal for buspirone reached a minimum indicating complete deprotonation of buspirone. Additional buspirone in THF (10–20 mL/g) was then charged to the reaction mixture in small increments until the IR signal indicated a 0.5% to 5% excess of buspirone. Air was sparged into the reaction mixture, controlling the initial rate of sparging so as to maintain the temperature of the reaction mixture less than –60° C. The sparging was continued until the reaction was complete as indicated by HPLC. Methyl tert-butyl ether (384.8 g, 4.365 mol, 520.0 mL) was added followed by 1M hydrochloric acid (1350.8 g, 1.328 mmol, 1328 mL) and the solution was warmed to ambient temperature. The pH was adjusted to between 6.5 and 6.9 using hydrochloric acid and $Na_3PO_4$. The phases were separated and the organic phase was washed twice with brine (542.3 g, 493 mL). The solvent of the rich organic layer was then replaced by isopropyl alcohol and the solution was cooled to crystallize the reaction product. There is an option to seed with 0.01 to 5% buspirone at approximately 54 to 56° C. The crystalline slurry was then filtered and the wet cake was washed with isopropyl alcohol and dried to provide 6-hydroxybuspirone (220.0 g, 82%), mp 109.5° C.

Alternatively the product can be crystallized by either of these two methods: (a) concentration and solvent replacement into heptane or hexanes, or (b) solvent replacement into EtOAc and crystallization by the combination of cooling and addition of heptane or hexanes.

EXAMPLE 2

Crystallization of 6-hydroxybuspirone to Reduce 6,10-dihydroxybuspirone and Buspirone 6-hydroxybuspirone (35.0 g, 90.8 mmol) was slurried with anisole (385 mL, 11 mL/g, 10–15 mL/g may be used). The mixture was heated to 80–100° C. and stirred to obtain a clear solution. The solution was then cooled to 75–85° C. before 6,10-dihydroxybuspirone seeds (87.5 mg, 0.25 wt %, 0–2 wt % may be used) were added. The mixture was then cooled to ambient temperature over 2–6 h and stirred overnight. The resulting slurry was filtered and the filtrate was concentrated to approximately half its initial volume. Heptane (400 mL) was then added over 1 h and the resulting slurry was stirred at ambient temperature overnight. The slurry was filtered and the resulting filter cake was washed with heptane. After drying, 23.04 g of 6-hydroxybuspirone was obtained (66% recovery). In some experiments, this recrystallization reduced 6,10-dihydroxybuspirone from ~9% to ~1.5%.

EXAMPLE 3

Crystallization of 6-hydroxybuspirone to Reduce Buspirone 6-hydroxybuspirone (220.0 g, 547.9 mmol) was slurried with absolute ethyl alcohol or isopropyl alcohol (2.20 L, 10 mL/g, 10–20 mL/g may be used) in a 3-necked round bottom flask equipped with a mechanical stirrer. The mixture was heated from ambient temperature to form a solution (55–70° C.). The resulting solution was then cooled to form a slurry. The solid was filtered, washed, and dried to provide purified 6-hydroxybuspirone (165.0 g, 75% recovery). In some experiments, this recrystallization reduced buspirone from ~3% to ~1.4%.

EXAMPLE 4

Alternate Protocol for 6-hydroxybuspirone

Buspirone (350.0 g, 0.908 mol) was dissolved in THF (6.9 L) in a 10 L vessel under argon. The mixture was cooled to −70° C. using a dry ice/IPA bath. A THF solution of NaHMDS (0.908 mol, 1.00 equiv [0.762 mol titrated to be 0.953 M and 0.146 mol titrated to be 0.91 M]) was added over 12 min while maintaining the temperature below −40° C. Triethylphosphite (3.18 mol, 3.5 equiv) was added in one portion over approximately one min. The solution was stirred at −60° C. for approximately 45 min. The solution was then cooled to −70° C. Oxygen (ultra high purity [UHP]) was bubbled into the reaction mixture using a gas dispersion tube. (Note: the bubbler and a Nitrogen inlet were configured so that nitrogen passed through the vessel during the entire reaction). An exotherm of approximately 5° C. was observed and the rate of oxygen sparging was controlled so as to maintain the temperature below −64.6° C. The reaction was monitored using HPLC by taking aliquots of the reaction mixture and quenching into the organic mobile phase. When the AP of the starting material no longer declined (AP approximately 2), the reaction was quenched with HCl (6 M, 0.5 L, the pH was measured to be approximately 3 at approximately −10° C.) and allowed to warm to room temperature overnight. The pH was adjusted to approximately 2.0 by the addition of NaOH (2 N, 40 mL) and the solution was observed to be cloudy and somewhat heterogeneous. HPLC analysis indicated 6-hydroxybuspirone (92.6 AP) and buspirone (1.27 AP). The mixture was transferred to a 22 L, jacketed 3-neck flask equipped with mechanical stirrer, gas adapter, reflux condenser, and thermocouple. Water was added (650 mL) and the mixture was heated. At approximately 35° C., the mixture became homogeneous. (Note: alternatively one can add 2.5 M HCl instead of 6 M HCl and water to adjust the pH to 2.0). The mixture was then warmed to approximately 58° C. for a total of approximately 30 h and held at ambient temperature for approximately 124 h. During the heating, samples were periodically taken for $^{31}$P NMR and HPLC analysis (monitoring for extent of hydrolysis of diethylphosphite to HP(O)(OH)(OEt) and HPLC analysis of 6-hydroxybuspirone).

The solution was then neutralized to a pH of 6.84 by the slow addition (25 min) of a NaOH/saturated brine solution (3.5 N, 1.0 L [700 mL of 10.0 N NaOH and saturated brine added until the volume reached 2.0 L]). MTBE (650 mL) and saturated brine (500 mL) were added in order to assist the phase split. The aqueous layer (2900 mL) was removed and saved for analysis and a sample of the organic layer was saved for analysis as well. To the organic layer was added saturated brine (650 mL) and MTBE (150 mL) and the phases were allowed to separate. The second aqueous layer was removed (800 mL) and saved for analysis. Samples of the phases were analyzed via $^{31}$P NMR (monitoring for diethylphosphite content) and HPLC (monitoring the amount of 6-hydroxybuspirone within a given phase).

A 4 L cylindrical, glass reactor equipped with mechanical stirrer, condenser, and thermocouples (for both batch and distillate temperature) was charged with 3800 mL of the solution. Distillation was conducted under reduced pressure (the pressure ranged from −19.5 to −20 in Hg) until the volume was approximately 500 mL. The remaining product-rich organic phase was added and distillation resumed, reducing the volume to approximately 1000 mL. IPA was added (2000 mL) and distillation at reduced pressure was resumed until the volume was reduced to approximately 1000 mL. An additional 1000 mL of IPA was added bringing the volume to approximately 2000 mL (no THF was detectable via GC and the water content was measured to be 0.13%). The mixture was heated to 75° C. to dissolve all solids and then subdivided into two batches detailed in A and B below.

Batch A. Approximately 1000 mL was transferred to a vessel equipped with a magnetic stirrer and water was added (15 mL, Karl Fischer titration indicated 3.94% water). This solution was then slowly cooled to ambient temperature while stirring, and seeded with 6-hydroxybuspirone (approximately 20 mg). The mixture was filtered seven days later on a 4–6 micron glass sintered filter and the mother liquor saved for analysis (740 mL). The off-white solid was subsequently washed with IPA (2×260 mL). The white solid was suctioned dried for 1 h and then placed into a an oven at 45° C. (27 in Hg with an N$_2$ bleed for 69 h). 6-Hydroxybuspirone was obtained as an off-white solid (166.0 g, purity=99 AP, buspirone AP=0.35, and a trans-diol side product AP=0.54).

Batch B. The remainder of the solution (water content 0.13%) was allowed to cool to ambient temperature and seeded with 6-hydroxybuspirone (20 mg) at approximately 56° C. The mixture was filtered seven days later on a 4–6 micron glass sintered filter and the reactor rinsed (four times with the mother liquor in order to recover all solids). The mother liquor was saved for analysis (620 mL). The off-white solid was subsequently washed with IPA (2×260 mL). The white solid was suctioned dried for 1 h and then placed into a an oven at 45° C. (27 in Hg with an $N_2$ bleed for 69 hours). 6-Hydroxybuspirone was obtained as an off-white solid (156.6 g, AP=99, buspirone AP=0.35, and a trans-diol side product AP=0.54).

EXAMPLE 5

3-Hydroxygepirone

Gepirone (4,4-dimethyl-1-[4-[4-(2-pyrimidinyl)-1-piperazinyl]butyl]-2,6-piperidinedione) (10.0 g, 27.8 mmol) was charged to a 500 mL flask equipped with a mechanical stirrer and a React-IR probe under inert gas. Tetrahydrofuran (250 mL, 25 mL/g) was charged and the mixture agitated at ambient temperature until homogeneous. Triethyl phosphite (28.9 g, 174 mmol, 29.8 mL, 6.25 eq) was added and the mixture was cooled to −65 to −80° C. The mixture was agitated at this temperature for at least 10 minutes to allow the React-IR signal to stabilize. 1.0 M Sodium bis (trimethylsilyl)amide in THF (27.8 mL, 27.8 mmol, 1.00 eq) was charged to the mixture at such a rate so as to maintain the temperature less than −60° C. Small amounts of sodium bis(trimethylsilyl)amide were charged to the mixture until the IR signal for buspirone reached a minimum indicating complete deprotonation of gepirone. Additional gepirone in THF (25 mL/g) was then charged to the reaction mixture in small increments until the IR signal indicated a 3.24% excess of gepirone. Air was sparged into the reaction mixture, controlling the initial rate of sparging so as to maintain the temperature of the reaction mixture less than −60° C. The sparging was continued until the reaction was complete as indicated by HPLC. Methyl tert-butyl ether (40.0 mL) was added followed by 1M hydrochloric acid (45.0 mL) and the solution was warmed to ambient temperature. The pH (9.48 at 20.6° C.) was adjusted to between 6.5 and 6.9 using hydrochloric acid and $Na_3PO_4$ (pH=6.95 at 22.7° C.). The phases were separated and the organic phase was washed twice with 25 wt % brine (40.0 mL). The solvent of the rich organic layer was then replaced by isopropyl alcohol and the solution was cooled to ambient temperature to crystallize the reaction product. The crystalline slurry was then filtered and the wet cake was washed twice with isopropyl alcohol (15.0 mL) and dried to provide 3-hydroxygepirone (9.32 g, 89%), mp 128° C.

We claim:
1. A process for preparing a hydroxyazapirones of Formula I,

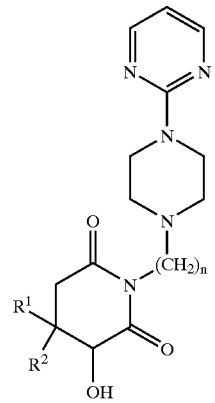

wherein
R$^1$ and R$^2$ are independently hydrogen, C$_{1-6}$alkyl, or
R$^1$ and R$^2$ taken together are —CH$_2$(CH$_2$)$_{0-5}$CH—, and
n is an integer from 2 to 5,
comprising reacting a compound of Formula III

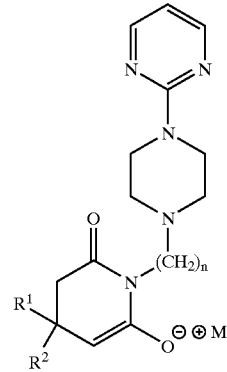

wherein M⊕ is an alkali earth metal cation
with molecular oxygen in the presence of a reductant to provide a Formula I product.
2. The process of claim 1 wherein the source of molecular oxygen is air or oxygen gas.
3. The process of claim 1 wherein the reductant is selected from the group consisting of triarylphosphites, trialkyl- and triaiyl phosphines, thiourea, sodium borohydride, copper (II) chloride with iron (II) sulfate, iron (III) chloride, titanium isopropoxide, dimethyl sulfide, dietyldisulfide, sodium sulfite, sodium thiosulfate, zinc and acetic acid, and 1-propene.
4. The process of claim 1 wherein the reductant is tri(C$_{1-8}$)alkylphosphite.
5. The process of claim 4 wherein the reductant is triethyl phosphite.
6. The process of claim 1 where R$^1$ and R$^2$ are independently selected from hydrogen and C$^{1-5}$alkyl.
7. The process of claim 6 where R$^1$ and R$^2$ are methyl and n is 4.

8. The process of claim 1 where $R^1$ and $R^2$ taken together are —$CH_2(CH_2)_{0-5}CH_2$—.

9. The process of claim 8 where $R^1$ and $R^2$ taken together are —$CH_2CH_2CH_2CH_2$— and n is 4.

10. A process for preparing a hydroxyazapirones of Formula I,

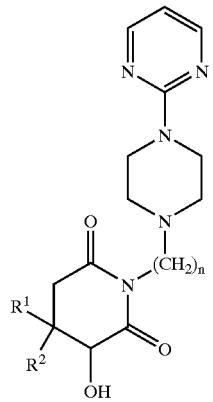

I wherein $R^1$ and R are independently hydrogen, $C_{1-6}$alkyl, or where $R^1$ and $R^2$ taken together are —$CH_2(CH_2)_{0-5}CH_2$—, and n is an integer from 2 to 5.

comprising (a) reacting an azapirone compound of Formula II

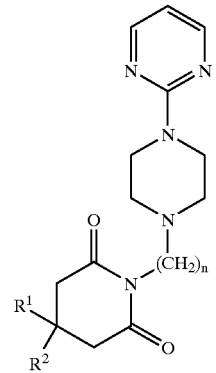

II with a strong base to form an intermediate imide enolate anion of Formula III where M⊕ is an alkali earth metal; and

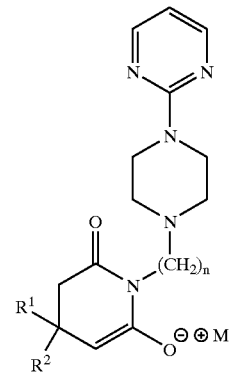

III (b) reacting the imide enolate III with molecular oxygen in the presence of a reductant.

11. The process of claim 10 wherein the source of molecular oxygen is air or oxygen gas.

12. The process of claim 10 wherein the afrong base is selected from the group consisting of lithium bis(trimethylsilyl)amide, sodium bis(trimethylsilyl)amide; potassium bis(trimethylsilyl)amide, lithium dialkylamide, sodium dialkylamide, potassium dialkylamide, sodamide, lithium alkoxide, sodium alkoxide, potassium alkoxide, lithium hydride, sodium hydride, and potassium hydride.

13. The process of claim 12 wherein the base is sodium bis(trimethylsilyl)amide.

14. The process of claim 10 wherein the imide enolate anion III formation is maximized by the use of spectroscopy monitor conversion of II to III.

15. The process of claim 14 wherein IR spectroscopy is used to monitor conversion of II to III.

16. The process of claim 10 wherein the reductant is selected from the group consisting of triarylphosphites, trialkyl- and triaryl phosphines, thiourea, sodium borohydride, copper (II) chloride with iron (II) sulfate, iron (III) chloride, titanium isopropoxide, dimethyl sulfide, diethyldisulfide, sodium sulfite, sodium thiosulfate, zinc and acetic acid, and 1-propene.

17. The process of claim 10 wherein the reductant is tri($C_{1-8}$)alkylphosphite.

18. The process of claim 17 wherein the reductant is triethyl phosphite.

19. The process of claim 1 where $R^1$ and $R^2$ are independently selected from hydrogen and $C_{1-6}$alkyl.

20. The process of claim 19 where $R^1$ and $R^2$ are methyl and n is 4.

21. The process of claim 10 where $R^1$ and $R^2$ taken together are —$CH_2(CH_2)_{0-5}CH_2$—.

22. The process of claim 21 where $R^1$ and $R^2$ taken together are —$CH_2CH_2CH_2CH_2$— and n is 4.

* * * * *